United States Patent
Adams et al.

(10) Patent No.: US 8,088,080 B2
(45) Date of Patent: ***Jan. 3, 2012

(54) MEDICAL INSTRUMENT

(75) Inventors: Leland Ray Adams, Ansonia, CT (US); Frederick Timothy Karl, Newtown, CT (US); Terence Clifford Johnson, Bloomington, IN (US); Hanspeter Robert Bayer, Meriden, CT (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/266,452

(22) Filed: Nov. 6, 2008

(65) Prior Publication Data

US 2009/0069713 A1    Mar. 12, 2009

Related U.S. Application Data

(63) Continuation of application No. 11/325,837, filed on Jan. 4, 2006, now Pat. No. 7,449,000, which is a continuation of application No. 10/300,512, filed on Nov. 20, 2002, now Pat. No. 7,008,382.

(51) Int. Cl.
  *A61B 10/00* (2006.01)
(52) U.S. Cl. ..................................................... 600/564
(58) Field of Classification Search .......... 600/562–568; 606/167, 170
See application file for complete search history.

(56) References Cited

U.S. PATENT DOCUMENTS

| | | | |
|---|---|---|---|
| 4,274,414 A | 6/1981 | Johnson et al. |
| 4,844,064 A | 7/1989 | Thimsen et al. |
| 4,924,878 A | 5/1990 | Nottke |
| 4,953,558 A | 9/1990 | Akerfeldt |
| 5,195,533 A | 3/1993 | Chin et al. |
| 5,368,045 A | 11/1994 | Clement et al. |
| 5,476,101 A | 12/1995 | Schramm et al. |
| 5,507,298 A | 4/1996 | Schramm et al. |
| 5,660,186 A | 8/1997 | Bachir |
| 5,685,852 A | 11/1997 | Turkel et al. |
| 5,718,237 A | 2/1998 | Haaga |
| 5,779,647 A | 7/1998 | Chau et al. |
| 5,842,999 A | 12/1998 | Pruitt et al. |
| 5,989,196 A | 11/1999 | Chu et al. |
| 5,993,399 A | 11/1999 | Pruitt et al. |
| 6,015,391 A | 1/2000 | Rishton et al. |
| 6,033,411 A | 3/2000 | Preissman |

(Continued)

FOREIGN PATENT DOCUMENTS

DE    100 34 297    4/2001

(Continued)

OTHER PUBLICATIONS

International Search Report issued on Apr. 22, 2004 in PCT application: PCT/US03/37595, filed on Nov. 20, 2003.

*Primary Examiner* — Brian Szmal
(74) *Attorney, Agent, or Firm* — Fish & Richardson P.C.

(57) ABSTRACT

A medical instrument includes a housing, a stylet having a portion in the housing, a cannula coaxially receiving the stylet and having a portion in the housing, and a member slidably coupled to the housing. The stylet and the cannula are movable between an extended position and a retracted position. The member is configured with first and second bars to move the stylet and the cannula from their extended positions to their retracted positions.

16 Claims, 11 Drawing Sheets

U.S. PATENT DOCUMENTS

| | | |
|---|---|---|
| 6,050,955 A | 4/2000 | Bryan et al. |
| 6,086,543 A | 7/2000 | Anderson et al. |
| 6,126,617 A | 10/2000 | Weilandt et al. |
| 6,142,955 A | 11/2000 | Farascioni et al. |
| 6,165,136 A | 12/2000 | Nishtala |
| 6,221,030 B1 | 4/2001 | Avaltroni |
| 6,293,957 B1 | 9/2001 | Peters et al. |
| 6,358,217 B1 | 3/2002 | Bourassa |
| 6,402,701 B1 | 6/2002 | Kaplan et al. |
| 6,428,486 B2 | 8/2002 | Ritchart et al. |
| 6,488,636 B2 | 12/2002 | Bryan et al. |
| 6,497,706 B1 | 12/2002 | Burbank et al. |
| 6,544,192 B2 | 4/2003 | Starr et al. |
| 6,620,111 B2 | 9/2003 | Stephens et al. |
| 6,730,045 B2 | 5/2004 | Finer |
| 6,849,080 B2 | 2/2005 | Lee et al. |
| 7,008,382 B2 | 3/2006 | Adams et al. |
| 7,022,085 B2 | 4/2006 | Cooke et al. |
| 7,201,722 B2 | 4/2007 | Krueger |
| 7,449,000 B2 * | 11/2008 | Adams et al. ........... 600/564 |
| 2008/0269638 A1 * | 10/2008 | Cooke et al. ........... 600/567 |

FOREIGN PATENT DOCUMENTS

| | | |
|---|---|---|
| EP | 0 536 888 | 4/1993 |
| JP | 1-198537 | 8/1989 |
| JP | 4-506758 | 11/1992 |
| JP | 6-197898 | 7/1994 |
| JP | 10-179592 | 7/1998 |
| JP | 2000-506044 | 5/2000 |
| JP | 2002-000609 | 1/2002 |
| JP | 2002-514458 | 5/2002 |

* cited by examiner

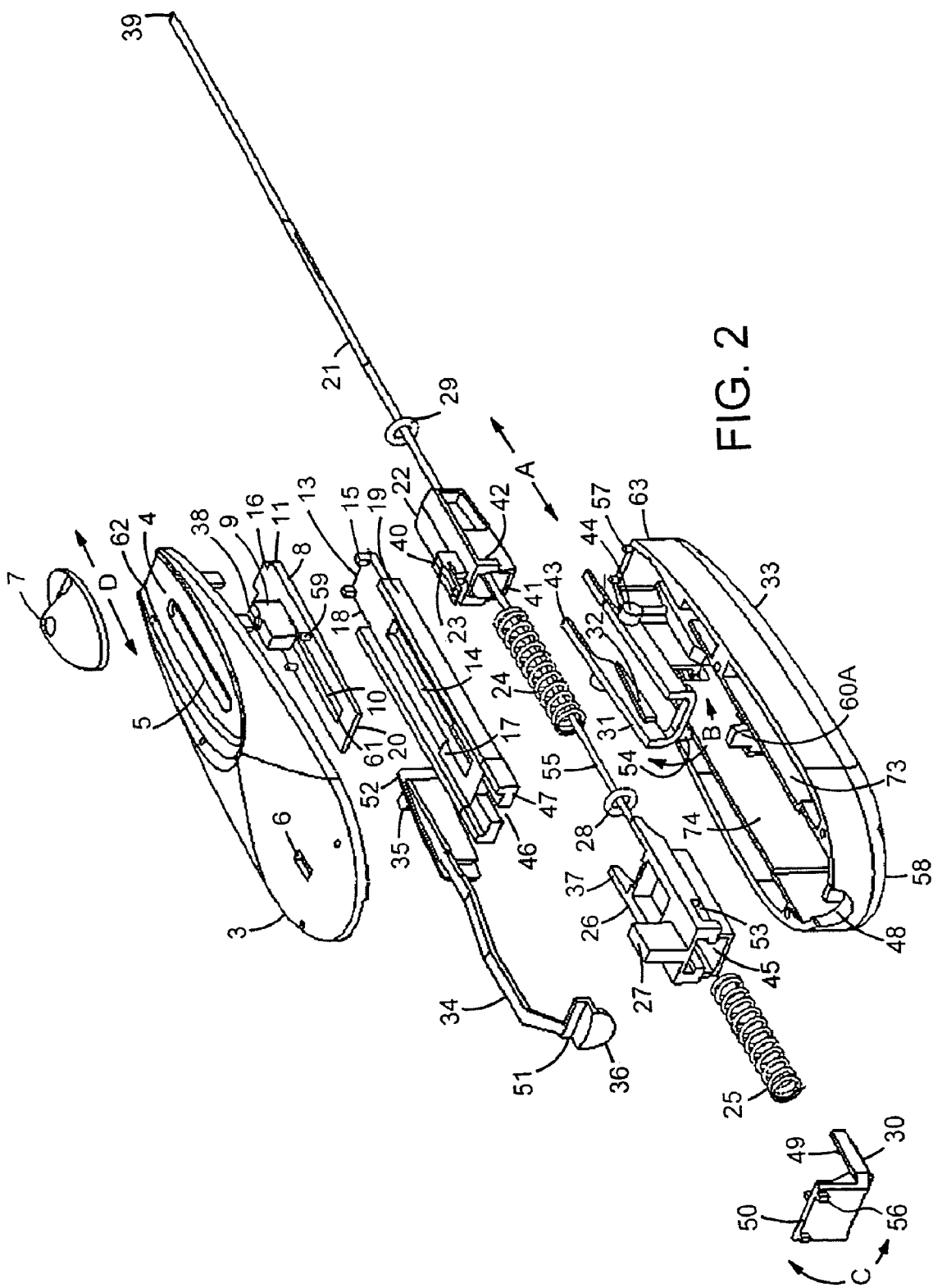

MEDICAL INSTRUMENT

CROSS-REFERENCE TO RELATED APPLICATIONS

This application is a continuation application of and claims priority to U.S. application Ser. No. 11/325,837, filed Jan. 4, 2006, which is a continuation application of and claims priority to U.S. application Ser. No. 10/300,512, filed Nov. 20, 2002, the entire contents of which being hereby fully incorporated by reference.

TECHNICAL FIELD

This invention relates to medical instruments.

BACKGROUND

A biopsy needle instrument can be used to obtain a tissue specimen for microscopic examination, e.g., to determine malignancy, while preferably subjecting the patient to the least trauma. In some embodiments, the instrument has of a long, thin probe, called a stylet, within a close-fitting hollow needle, called a cannula. The stylet has a notch into which tissue can prolapse when the stylet enters the tissue.

During use, a firing device first projects the stylet into tissue, followed immediately by the cannula. As the cannula slides over the stylet, the cannula severs from the surrounding mass tissue that has prolapsed into the notch of the stylet, and captures the prolapsed tissue as a specimen within the notch. The instrument can then be withdrawn and the piece of tissue removed from the stylet.

SUMMARY

In one aspect, the invention features a medical instrument that includes a housing, a stylet, a cannula, and a member (e.g., a cocking member). The stylet is movable between an extended position and a retracted position. The cannula coaxially receives the stylet and is movable between its extended position and retracted position. The member is coupled, e.g., mounted on or connected directly or indirectly, to the housing, and is capable of moving the stylet from the extended position to the retracted position, and when separately engaged, moving the cannula from the extended position to the retracted position. The member can include a button, and the member can be engaged by a user's hand, e.g., palm and/or finger(s).

Embodiments of the aspect of the invention may include one or more of the features described above and below, in any combination.

In another aspect, the invention features a medical instrument that includes a housing, a stylet, a cannula, and a member, e.g., a cocking member. The stylet is movable between an extended position and a retracted position. The cannula coaxially receives the stylet and is movable between its extended position and retracted position. The member is slidably coupled to the housing, and is configured such that when a user engages the member (e.g., two times), the cannula is moved from an extended position to a retracted position and the stylet is moved from an extended position to a retracted position, in a sequential manner. The member can be configured such that the cannula is moved from an extended position to a retracted position when a user engages the member a first time, and the stylet is moved from an extended position to a retracted position when a user engages the member a second time. The member can also be configured such that the stylet is moved from an extended position to a retracted position when a user engages the member a first time, and the cannula is moved from an extended position to a retracted position when a user engages the member a second time.

In some embodiments, the instrument can further include a cannula block that includes at least one (e.g., two, three, or more) retentive portion(s) capable of holding the cannula in the retracted position. The cannula block is attached to a proximal end of the cannula. The instrument can also include a cannula block receiver which includes at least one (e.g., two, three or more) locking surfaces, wherein the locking surface(s) engages, e.g., locks into, the retentive portion(s) of the cannula block when the cannula is in the retracted position.

The instrument can also include a primary bar coupled, e.g., attached by a linkage, to the member. The primary bar is engageable with the cannula block to move the cannula block and cannula to the retracted position. In some embodiments, the primary bar is capable of being in a first position in which the primary bar is engageable with the cannula block to move the cannula block and cannula to the retracted position without moving the stylet block, and in a second position in which the primary bar is engageable with a secondary bar to move the stylet block and stylet to the retracted position.

In some embodiments, the instrument can include a stylet block attached to the stylet, and a stylet block receiver. The stylet block receiver and stylet block can engage when the stylet is in the retracted position. The instrument can include a secondary bar engagable with the stylet block and adapted to move the stylet block and stylet to the retracted position. Further, the instrument can include a first trigger engageable with the stylet block receiver to release the stylet from the retracted position. The first trigger can be located on the housing, e.g., the proximal end of the housing, and can pivotally move the stylet block receiver to disengage the stylet block receiver from the stylet block. In some embodiments, the instrument can include a second trigger also being configured to release the stylet from the retracted position.

In other embodiments, the instrument can include an indicator that indicates when the stylet is in the second retracted position.

In another aspect, the invention features a medical instrument that includes a housing, a stylet having a portion in the housing and movable between an extended position and a retracted position, a stylet block attached to a proximal end of the stylet, a cannula coaxially receiving the stylet and having a portion in the housing, the cannula being movable between an extended position and a retracted position, a cannula block attached to a proximal end of the cannula, a member slidably coupled to the housing, a secondary bar within the housing and capable of moving the stylet block from an extended position to a retracted position, and a primary bar within the housing and coupled to the member. The primary bar is capable of being in a first position in which the primary bar is engageable with the cannula block to move the cannula block and cannula to the retracted position without moving the stylet block, and in a second position in which the primary bar is engageable with the secondary bar to move the stylet block and stylet to the retracted position.

In some embodiments, the medical instrument can include a trigger mechanism that includes a first trigger element that has a first trigger, and a second trigger element that has a second trigger, wherein the second trigger element is configured to retain the stylet block and stylet in the retracted position, and wherein the first and second trigger elements are engagable such that the stylet block and stylet are released from the retracted position when the first or second trigger is engaged.

In still another aspect, the invention features a medical instrument that includes a housing, a stylet, a cannula, and a member, e.g., a cocking member, and an indicator. The stylet is movable between an extended position and a retracted position. The cannula coaxially receives the stylet and is movable between its extended position and retracted position. The member is slidably coupled to the housing, and is configured such that when a user engages the member (e.g., two times), the cannula is moved from an extended position to a retracted position and the stylet is moved from an extended position to a retracted position, in a sequential manner. The indicator is associated with the housing, and provides a visual indication of the position of the stylet by a change, e.g., in color or symbol.

In another aspect, the invention features a medical instrument that includes a housing, a stylet, a cannula, and a member slidably coupled to the housing. The stylet is movable between an extended position and a retracted position. The cannula coaxially receives the stylet and is movable between its extended position and retracted position. The member is slidably coupled to the housing, and is configured to move the cannula from the extended position to the retracted position and, during a separate engagement by a user, to move the stylet from the extended position to the retracted position.

In yet another aspect, the present invention features a method of taking a biopsy sample from a patient. The method includes providing a medical instrument of the present invention, engaging the member a first instance to move the cannula from an extended position to a retracted position, engaging the member a second instance to move the stylet from an extended position to a retracted position, placing a distal end of the cannula against a patient, and activating, e.g., firing, the medical instrument. The instrument can be engaged using at least one trigger to release the stylet from the second retracted position. The invention also features using the medical instrument on a patient, e.g., a human, in a medical procedure.

Embodiments may have one or more of the following advantages. The instrument can be relatively easy to load prior to firing the instrument. The member of the instrument provides good mechanical advantage and is used to load the stylet and the cannula with the same motion. The instrument can include two trigger mechanisms, which enhances the versatility and convenience of the instrument. For example, depending on a target site and/or preference of a user, a radiologist can prefer to use a side trigger, while a urologist can prefer the rear trigger.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 is an exploded, perspective view of the biopsy instrument of FIG. 1.

DETAILED DESCRIPTION

Figure 1:
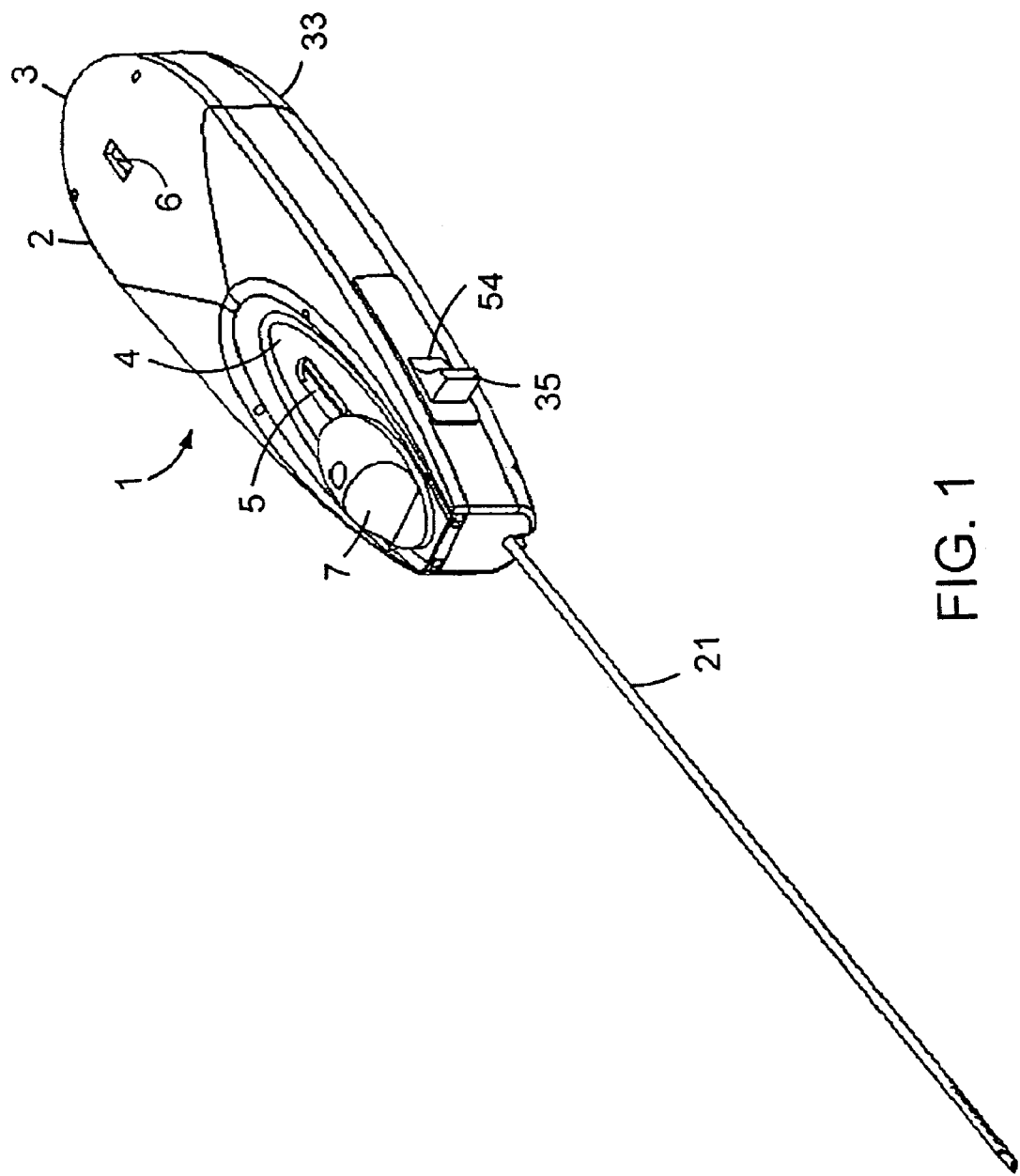
FIG. 1 is a perspective view of an embodiment of a biopsy instrument.
Figure 3A:
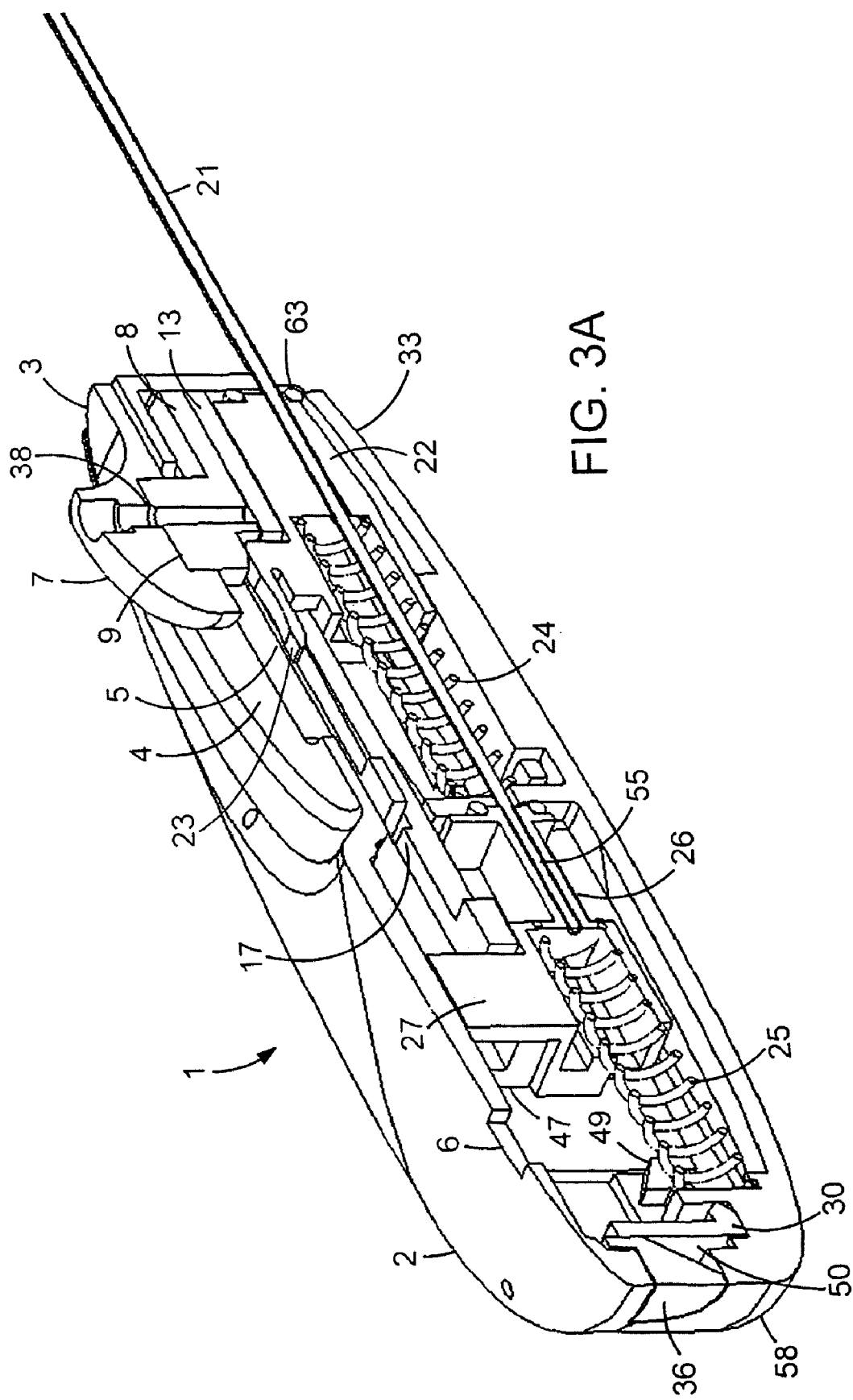
FIGS. 3A-D illustrate the biopsy instrument of FIG. 1 at various stages of operation.

Referring to FIGS. 1, 2, and 3A, a biopsy instrument 1 includes a housing 2, a stylet 55, a cannula 21, a member 7 slidably coupled to the housing 2, a side trigger 35, and a rear trigger 36. Housing 2 includes a top shell 3 and a bottom shell 33 (as shown in Figures) that are bonded together. Stylet 55 and cannula 21 have portions located within housing 2 and are configured to be axially movable relative to each other, between retracted positions and extended positions. As shown in FIG. 3A, stylet 55 and cannula 21 are in their extended positions. During use, stylet 55 and cannula 21 are loaded or cocked to their retracted positions, ready to be triggered. When stylet 55 and cannula 21 are triggered, they rapidly move distally to their extended positions, e.g., to collect a tissue specimen that has prolapsed into a notch (not shown) located near the distal end of stylet 55. Member 7 is connected to primary bar attachment element 9 of the primary bar 8 via a linkage 38. Overall, member 7 and primary bar 8 are parts of a mechanism that is used to load both stylet 55 and cannula 21 to their retracted positions. Specifically, member 7 and primary bar 8 together move cannula 21 to its retracted position and member 7, primary bar 8, and secondary bar 13 together move stylet 55 to its retracted position. After stylet 55 and cannula 21 are loaded, either side trigger 35 or rear trigger 36 can be used to release the stylet and the cannula to their extended positions.

Referring to FIGS. 2 and 3A, cannula 21 is generally a hollow sheath, e.g., made of stainless steel, that receives stylet 55, which can also be made of stainless steel. At its distal end 39, cannula 21 is configured to sever tissue that has prolapsed into a notch (not shown) formed with at the distal end of stylet 55. Cannula 21 extends into housing 2 wherein the cannula is attached to an axially movable (arrow A) cannula block 22.

Cannula block 22 includes a cannula block hook 23, which extends through primary bar elongate perforation 10 and secondary bar elongate perforation 14 when instrument 1 is assembled. Cannula block hook 23 is engaged at its rear surface 40 by primary bar attachment element 9 during use (described below). Cannula block first raised portion 23 also engages primary bar 8 at its proximal end 20 of primary bar 8 (described below). Cannula block 22 also includes an orifice 41 adapted to receive a first compression spring 24, e.g., a stainless steel spring, e.g., having a spring rate of 9.77 lb/in, and two cannula block retentive portions 42. First compression spring 24 engages cannula block 22 and biases cannula block 22 distally. Cannula block retentive portions 42 are raised portions on either side of cannula block 22, and are adapted to engage cannula block receiver 31 and cannula block receiver locking surfaces 32.

Cannula block receiver 31 can be, e.g., a prong-shaped element having two arms 43 adapted to receive cannula block 22. Cannula block receiver is pivotally attached to bottom shell 33 by linkages 44, which allow cannula block receiver 31 to pivot (arrow B). Cannula block receiver also includes cannula block receiver locking surfaces 32, which are, e.g., raised and angled surfaces adapted to guide cannula block 22 into cannula block receiver 31, and to engage cannula block retentive portions 42.

Stylet 55 is slidably and coaxially located in cannula 21. Stylet 55 has a distal end (not shown) configured to penetrate tissue and a notch (not shown) for collecting a tissue sample. Examples of suitable stylet 55 and cannula 21 configurations are exemplified by the ASAP™ Automated Biopsy System having a Delta Cut® needle or a Channel Cut® needle (available from Boston Scientific Corp., Natick, Mass.), and described in Chu, U.S. Pat. No. 5,989,196, hereby incorporated by reference. From distal end (not shown), stylet 55 extends into housing 2 where stylet 55 is attached to an axially movable stylet block 26.

Stylet block 26 includes two arms 37, which are adapted to contact cannula block receiver 31 around stop block 60A of bottom shell 33 during firing of the instrument (described below). Stylet block 26 also includes a stylet block raised portion 27, which is adapted to be received between the arms 47 of secondary bar 13. Stylet block 26 also includes an orifice 45 adapted to receive a second compression spring 25, e.g., a stainless steel spring having a spring rate of 9.77 lb/in, and two stylet block retentive portions 53, e.g., notches adapted to be received by stylet block receiver 30 and stylet block locking surfaces 49.

Stylet block receiver 30 is pivotally attached to bottom shell 33 by linkages (not shown), which allow stylet block receiver 30 to pivot (arrow C). Stylet block receiver 30 is a generally L-shaped element that includes a rear surface 50 that can contact rear trigger 36 on trigger bar 34. Stylet block receiver 30 also includes stylet block locking surfaces 49, which are, e.g., raised and angled surfaces adapted to guide stylet block 26 into stylet block receiver 30 and to engage stylet block retentive portions 53. Stylet block receiver can also include two raised surfaces 56 on rear surface 50 of stylet block receiver 30, which can be configured to receive rear trigger 36.

Trigger bar 34 is a generally elongate element having a rear trigger 36 at its proximal end 51 and a side trigger 35 near its distal end 52. Rear trigger 36 is, e.g., a portion of trigger bar 34 formed in the shape of tab or button. Rear trigger 36 is adapted to contact rear surface 50 of stylet block receiver 30. Side trigger 35 can also be a portion of trigger bar 34 formed in the shape of tab or button.

Figure 4A:
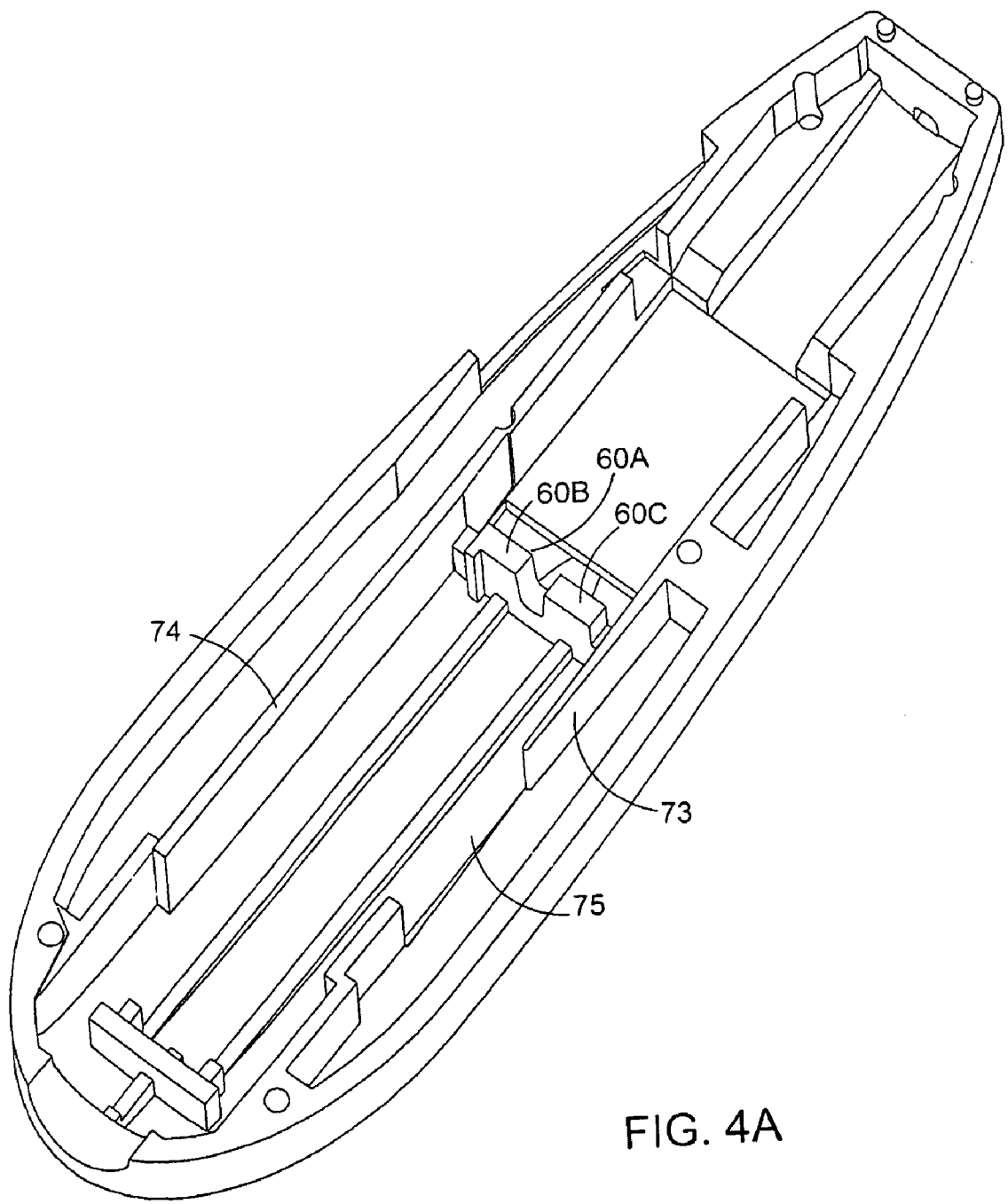
FIGS. 4A-4B is an enlarged view of an embodiment of the present invention.
Figure 4B:
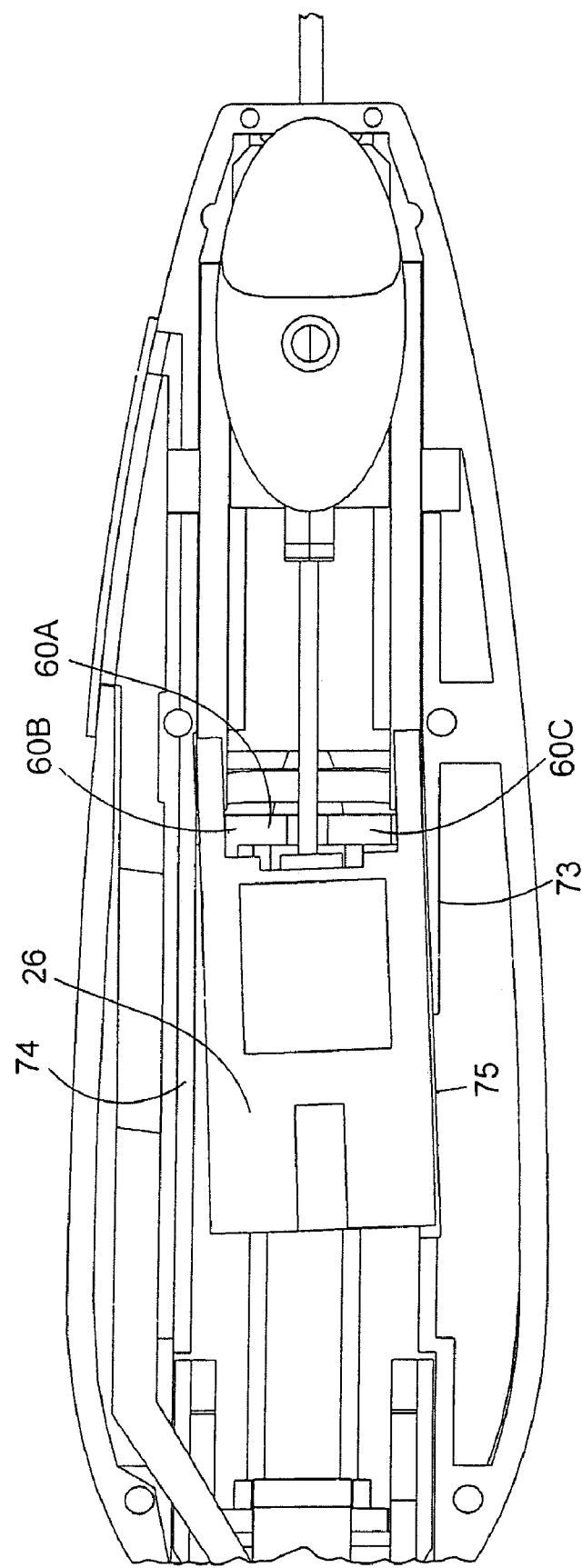

Bottom shell 33 of housing 2 includes stop block 60A, which is situated proximally to cannula block receiver. Bottom shell 33 can also include first 73 and second 74 walls formed therein, between which stylet block 26 and/or cannula block 22 move during operation of instrument 1. FIGS. 4A and 4B illustrate one embodiment of stop block 60A. Referring to FIG. 4A, stop block 60A can be formed such that one side (e.g., 60B) of stop block 60A is slightly thicker, e.g., about ⅛$^{th}$ of an inch thicker, than the other side (e.g., 60C), of stop block 60A. In such an embodiment, when stylet block 26 contacts stop block 60A (see FIG. 4B), stylet block 26 rotates slightly to cause friction between stylet 24 and cannula 21, decreasing or preventing recoil of stylet block 26 during firing of the instrument (described below). Accordingly, wall 73 can include a gap 75, which allows stylet block 26 to rotate between first wall 73 and second wall 74 (see FIG. 4B).

Bottom shell 33 includes a first recessed portion 48 or perforation at its proximal end 58 adapted to receive rear trigger 36, and a second recessed portion 54 or perforation adapted to receive side trigger 35. Bottom shell 33 can also include raised portions 57 at distal end 63 of the bottom shell. In some embodiments of the present invention, these raised portions can be used for joining primary bar 8 to bottom shell 33 by at least one (e.g., two) spring(s) (not shown). Specifically, spring(s) (not shown) can be connected to raised portions 57 on bottom shell 33 at one end, with the other end of the spring(s) (not shown) being attached to optional raised portions 59 on primary bar 8. The inclusion of springs connecting primary bar 8 and bottom shell 33 results in the primary bar 8 being biased toward the distal end 62 of top shell 3.

Top shell 3 of housing 2 includes a recessed portion 4 adapted to allow member 7 to slide longitudinally (arrow D) within the recessed portion. Member 7 can take any shape, e.g., a formed button, tab, or finger grip. Top shell 3 also includes elongate perforation 5, through which member 7 and primary bar attachment element 9 are connected by linkage 38. Top shell 3 can also include at least one perforation, e.g., window 6, which can be utilized as an indicator (described below).

Primary bar 8 includes primary bar attachment element 9, which serves, in part, to attach primary bar 8 to member 7 via linkage 38. Primary bar 8 also has a surface 12 that can contact rear surface 40 of cannula block hook 23. Primary bar 8 also includes two recessed portions 11 at its distal end 16, which are adapted to engage secondary bar raised portions 15 during use of the instrument. Primary bar 8 also includes an elongate perforation 10 through which cannula block hook 23 extends.

Secondary bar 13 includes secondary bar raised portions 15, adapted to be received by primary bar recessed portions 11. At proximal end 46, secondary bar 13 includes two arms 47 adapted to engage and receive stylet block raised portion 27 during use of the instrument. Secondary bar also includes also includes an elongate perforation 14 (through which cannula block hook 23 extends), and secondary bar stops 17. Secondary bar also includes guide surfaces 19 adapted to receive and guide primary bar in a slidable manner during use of the instrument.

In some embodiments of the present invention, instrument 1 includes a first 29 and/or a second 28 O-ring, which can act to absorb shock, thus affording more comfort to the user (e.g., by decreasing vibration) and decreasing sound that emanates from the instrument during use.

In some embodiments, window 6 in top shell 3 can act as a visual indicator (or as part of a visual indication system), which signals when stylet 55 is in its retracted position (loaded position). The indication system can include one or more perforations (e.g., window 6 in top shell 4) formed in housing 2 that allow a user to detect a change in the position of stylet block 26. For example, perforation(s) can be formed on housing 2 such that stylet block raised portion 27 covers the window(s) when the stylet block 26 is in its extended position. When stylet block 26 is retracted, stylet block raised portion 27 slides away from window(s) and uncovers interior portions of instrument 1. The interior portions can be colored, e.g., red, for enhanced visibility. In other embodiments, perforation 6 can be aligned with stylet block raised portion 27 which has a first color, e.g., red, and the interior portions can have a second color, e.g., green. When stylet block 52 is moved from its extended position to its retracted position, the color visible through window(s) changes from the second color to the first color to indicate that instrument 1 is loaded. Alternatively or in addition, instrument 1 can include a perforation(s) in housing 2 aligned with cannula block 23 to indicate the position of the cannula block. For example, cannula block 23 can be formed with portions with different colors as described above.

FIGS. 3A-3D illustrate a sequence of the operation of instrument 1. Referring to FIG. 3A, instrument 1 is in its rest position, e.g., as taken out of its packaging. Cannula block 22 and stylet block 26 are at their most distal, extended positions. Member 7 and both primary 8 and secondary 13 bars are in a distal position.

Figure 3B:
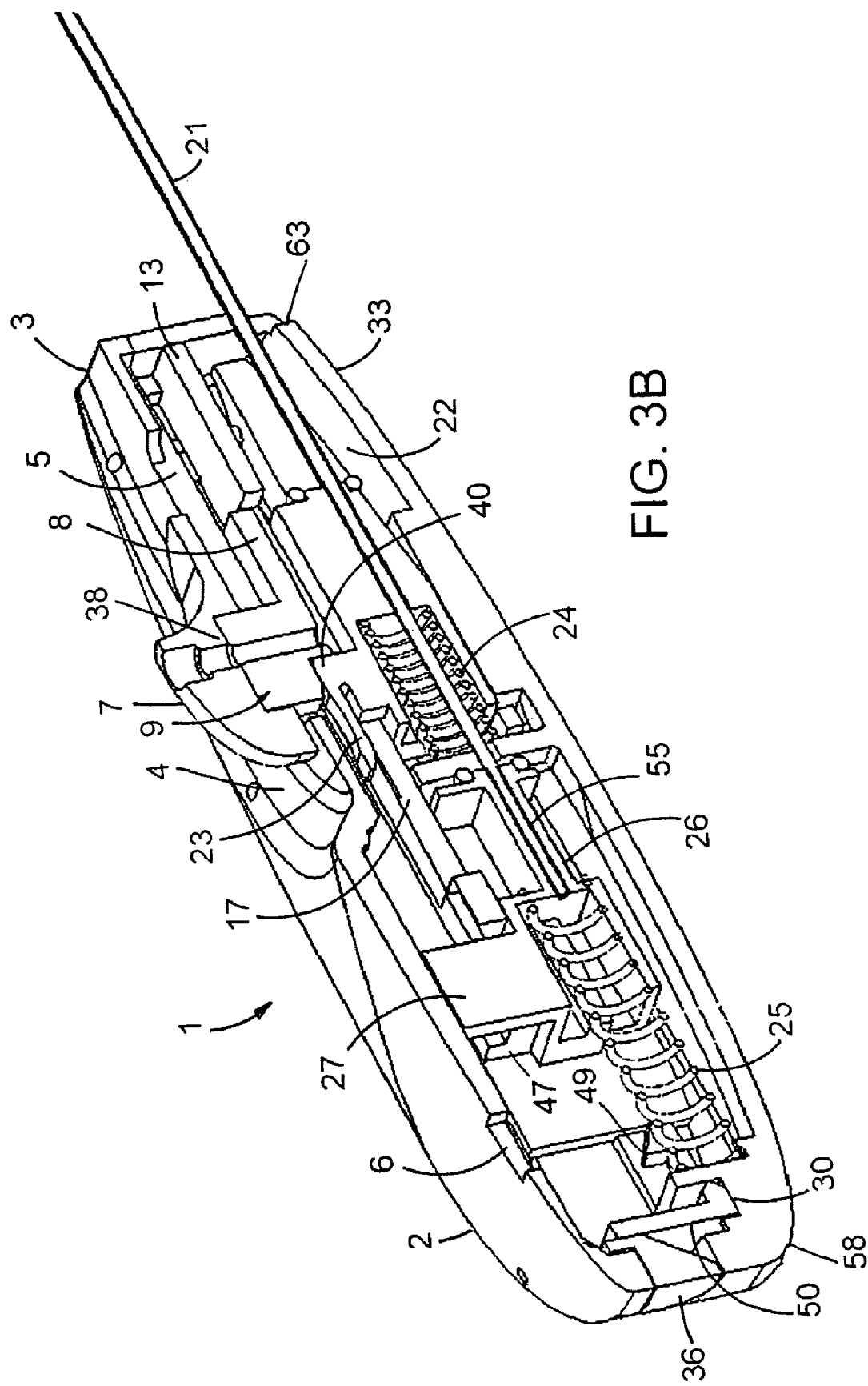

To load or move cannula block 22 and stylet block 26 to their retracted positions, member 7 is engaged, e.g., moved (cocked) toward the proximal end of instrument 1, two times. Referring to FIG. 3B, when member 7 is engaged the first time, primary bar 8 contacts rear surface 40 of cannula block hook 23, and both primary bar 8 and cannula block 22 are moved in a proximal direction. As a result, cannula block 22 and cannula 21 are pushed proximally until cannula block retentive portions 42 engage cannula block receiver locking surfaces 32. As cannula block receiver 31 receives cannula block 22, cannula block receiver 31 rotates (arrow B) to allow cannula block retentive portions 42 to engage cannula block receiver locking surfaces 32. Cannula block receiver arms 43 press against top shell 3 to bias the rotation of cannula block receiver 31 to a clockwise (arrow B) direction. Once cannula block receiver locking surfaces engage, e.g., lock into, cannula block retentive portions 42, the cannula block 22 and cannula 21 remain in their retracted positions (FIG. 3B). In this position, first compression spring 24 is compressed between cannula block 22 and stop block 60A in bottom shell 33. Member 7 is then released by the user and allowed to return to its distal position, e.g., aided by a spring (not shown).

Figure 3C:
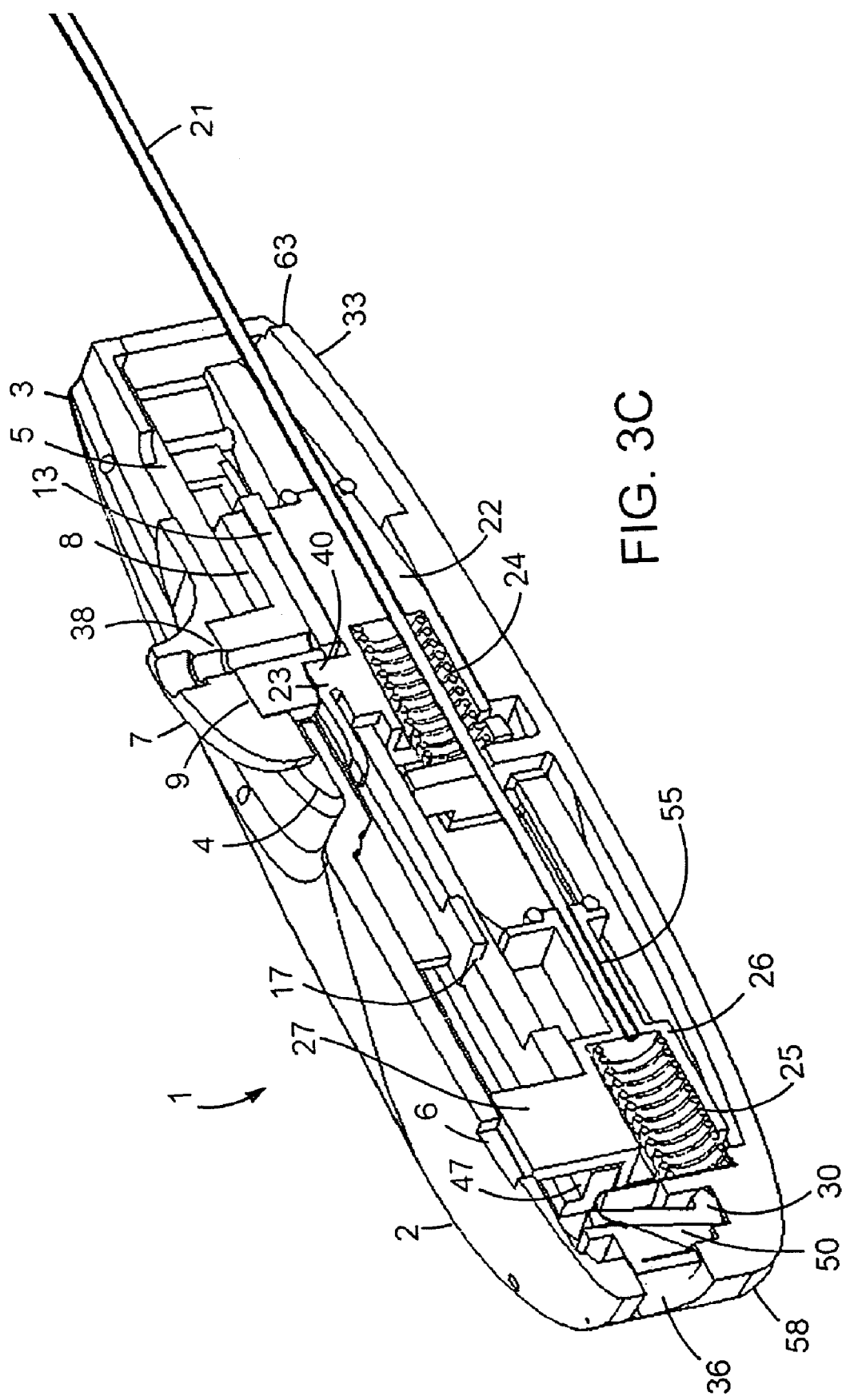
Figure 3D:
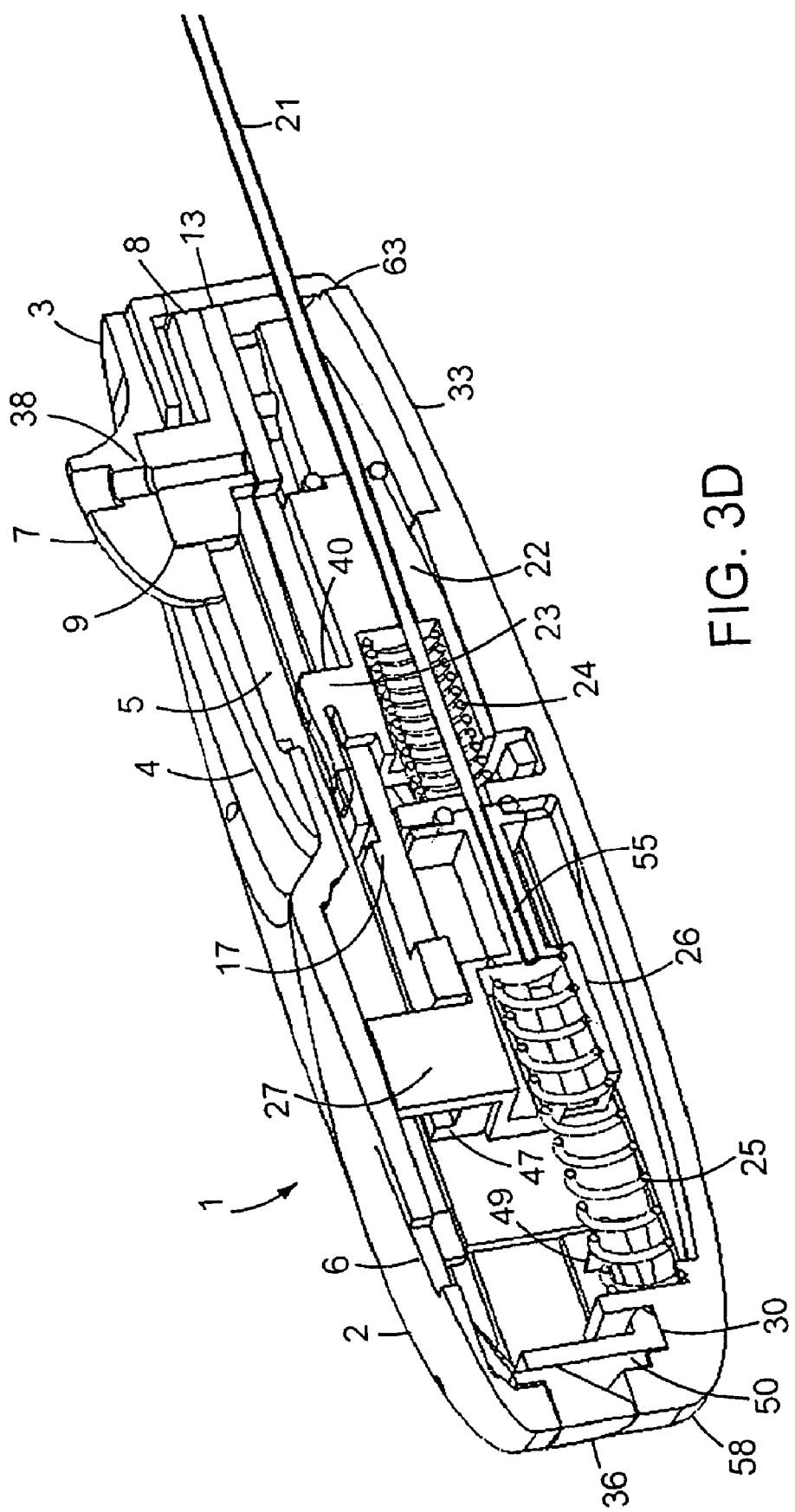

When member 7 is engaged the first time, primary bar 8 is in a first position and not aligned with stops 17 on secondary bar 14. As a result, during the first actuation of member 7, primary bar can slide over stops 17. However, as member 7 and primary bar 8 return to their distal position after the first actuation, cannula block hook 23 engages surface 61 at proximal end 20 of primary bar 8. When cannula block hook 23 engages surface 61, primary bar rotates or flexes slightly to a second position, such that proximal end 20 of primary bar 8 aligns with stops 17 of secondary bar 13. As a result, member 7, primary 8 and secondary 13 bars all move together when member 7 is engaged a second time. Specifically, when member 7 is engaged a second time, primary bar 8 contacts rear surface 40 of cannula block hook 23, proximal end 20 of primary bar 8 contacts secondary bar stops 17, and secondary bar 13 arms engage stylet block raised portion 27. As a result, stylet block 26 and stylet 55 are pushed proximally until stylet block retentive portions 53 engage stylet block receiver 30 and stylet block receiver locking surfaces 49. Once stylet block receiver locking surfaces 49 engage, e.g., lock into, stylet block receiver locking surfaces 49, stylet block 26 and stylet 55 remain in their retracted positions (FIG. 3C). In this position, second compression spring 25 is compressed between stylet block 26 and stylet block receiver 30. Referring to FIG. 3C, both cannula 21 and stylet 55 are fully cocked and prepared for use. Cannula block 22 and stylet block 26 are at their most proximal, retracted positions. Instrument 1 cocked and ready to be triggered or fired.

To fire instrument 1, distal end of stylet (not shown) is placed adjacent to a target area, and either side trigger 35 or rear trigger 36 is engaged. To engage rear trigger 36, the rear trigger is pushed distally, e.g., using an index finger, which causes rear trigger 36 to push rear surface 50 of stylet block receiver 30. As a result, stylet block receiver 30 pivots (arrow C) to disengage stylet block retentive portions 53 from stylet block receiver locking surfaces 49. Upon disengagement, stylet block 26 and stylet 55 are propelled distally by the spring force of second compression spring 25, which allows stylet 55 to penetrate the targeted area. Stylet block 26 then strikes cannula block receiver 31 (FIG. 3D), causing it to pivot (arrow B) to disengage cannula block retentive portions 42 from cannula block receiver locking surfaces 32. Upon disengagement, cannula block 22 and cannula 21 are propelled distally by the spring force of second compression spring 24, which allows cannula 21 to slide over stylet 55 and to sever a specimen that has prolapsed into notch (not shown) within stylet 55.

Instrument 1 can then be withdrawn. The specimen can be removed from stylet notch (not shown) by engaging member 7 once to retract cannula 21 and expose stylet 55. The specimen can be placed on a slide or in a preservative solution. If desired, member 7 can be engaged to retract and load stylet 55 to collect another specimen.

Side trigger 35 is engaged by pushing the side trigger 35 distally, e.g., using an index finger, which causes trigger bar 34 to move distally as well. Accordingly, rear trigger 36 also moves distally, which causes instrument 1 to fire as described above.

Figure 5A:
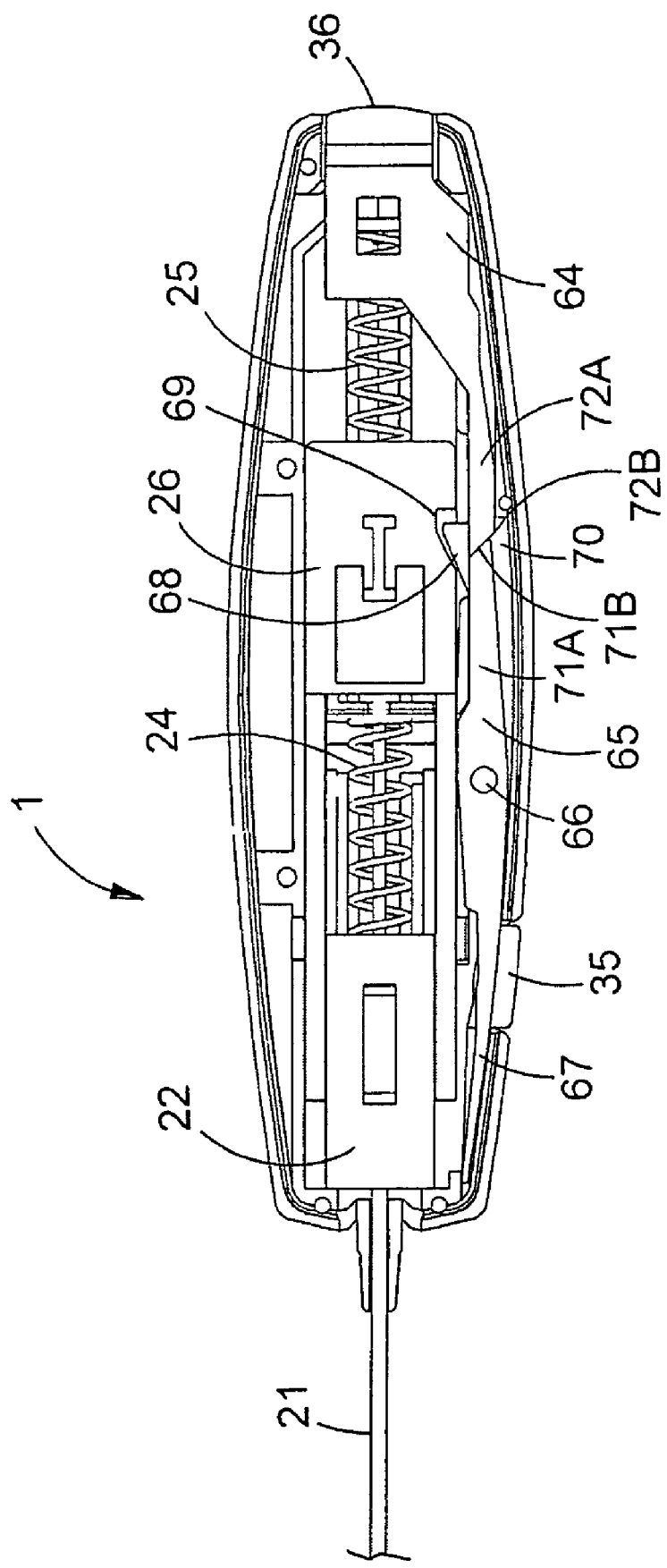
FIGS. 5A-5C illustrate an alternative embodiment of the biopsy instrument at various stages of operation.
Figure 5B:
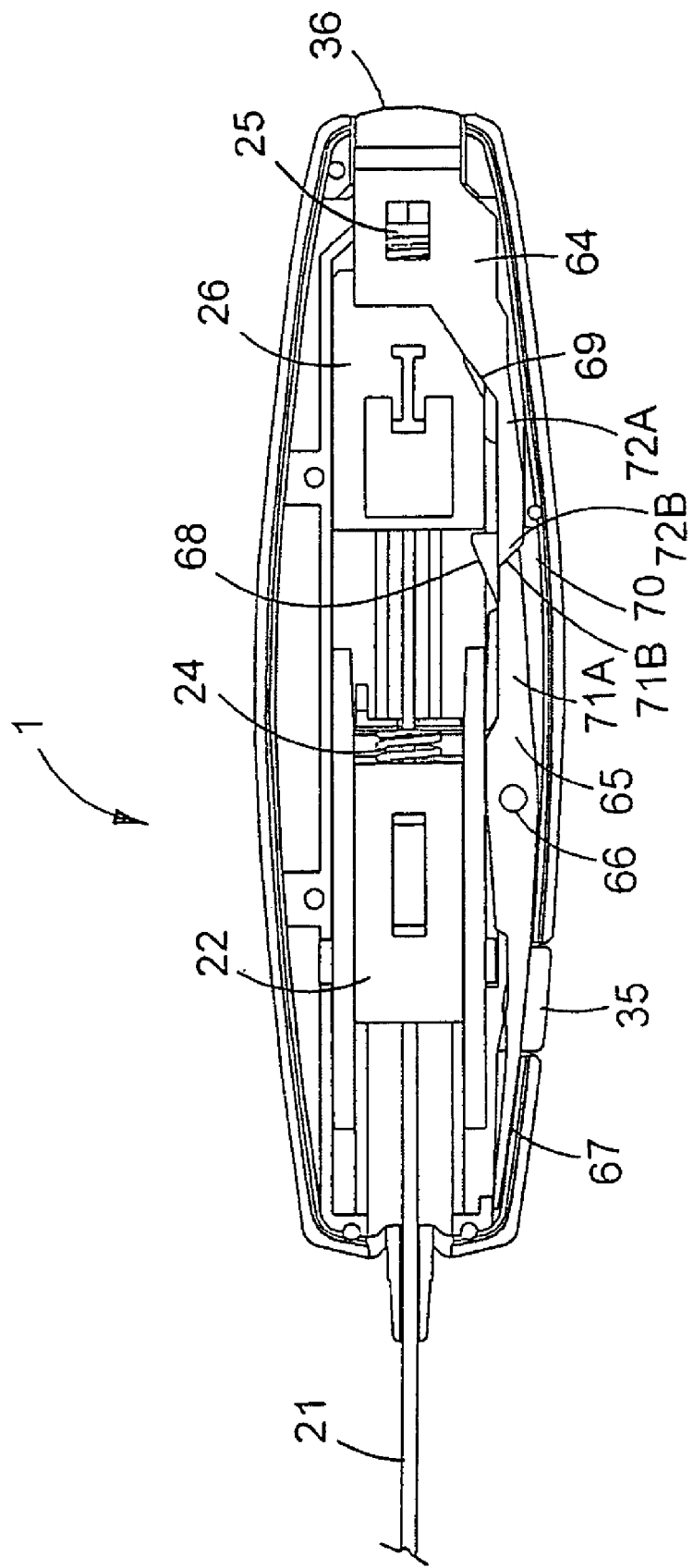
Figure 5C:
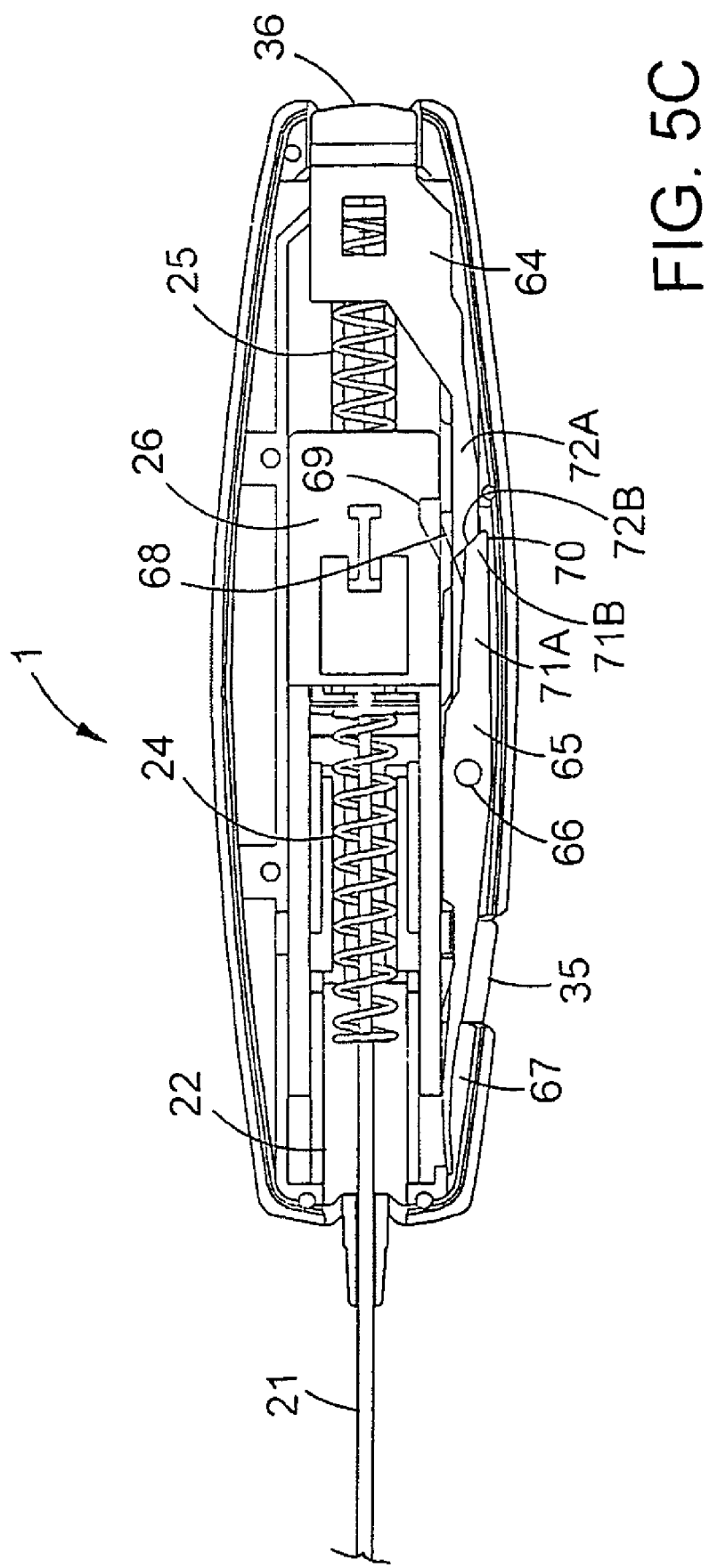

FIGS. 5A-5C illustrate an alternative embodiment of the present invention, wherein biopsy instrument 1 includes an alternative firing mechanism. Referring to FIG. 5A, wherein instrument 1 is in a resting position, trigger bar 34 is replaced with a firing mechanism that includes rear trigger element 64 and side trigger element 65. Rear trigger element 64 includes rear trigger 36 and rear trigger element angled end 72A. Rear trigger element angled end 72A includes an angled surface 72B. Angled surface 72B is adapted to contact another angled surface, angled surface 71B, of side trigger element 65 at junction 70. Side trigger element 65 includes side trigger 35 and side trigger element angled end 71A. Side trigger element angled end 71A includes angled surface 71B. Angled surface 71B is adapted to contact angled surface 72B at junction 70. Side trigger element 65 also includes retentive portion 68, which is adapted to contact and retain stylet block 25 in a cocked position when biopsy instrument 1 is loaded (see FIG. 5B). In this embodiment, stylet block 26 includes stylet block notch 69, which is engaged by retentive portion 68 when biopsy instrument 1 is at rest (e.g., after firing). Retentive portion 68 is located next to angled surface 71B at side trigger element angled end 71A. Side trigger element 65 also includes side trigger element pivot 66 and leaf spring end 67. Side trigger element can be pivotally connected to bottom shell 33.

In this alternative embodiment, the instrument 1 is cocked in a manner similar to that described above, i.e., member 7 is engaged two times. Referring to FIG. 5C (wherein instrument 1 is illustrated in the process of firing), instrument 1 can be fired using either side trigger 35 or rear trigger 36. To engage rear trigger 36, rear trigger is pushed (leftward in FIG. 5C), e.g., using an index finger, which causes rear trigger element 64 to move in the same direction (leftward in FIG. 5C). This motion causes angled surface 72B to slide against angled surface 71B at junction 70, causing side trigger element 65 and retentive portion 68 to rotate about pivot 66, disengaging retentive portion 68 from stylet block 26. Stylet 55 and cannula 21 are then discharged and propelled forward as described above.

To fire the instrument using side trigger 35, the side trigger is pushed (upward in FIG. 5C) e.g., using an index finger, which causes side trigger element angled end 71B and retentive portion 68 to rotate about pivot 66, disengaging retentive portion 68 from stylet block 26. The instrument then discharges as described above. Leaf spring end 67 biases retentive element 68 to a resting position (see FIGS. 5A and 5B).

In some embodiments, housing 2 and/or member 7 can each be made of different materials, e.g., to enhance the grip or "feel" of instrument 1. For example, housing 2 and/or member 7 can be formed of materials with different hardness, e.g., a core of relatively hard material and an outer layer of relatively soft material. The outer layer can be a foamy material, such as a urethane, to enhance the grip and/or to absorb vibrations from the firing of instrument 1. Each of housing 2 and/or member 7 can be formed with two or more different materials.

The components of instrument 1 described above can be formed by conventional injection molding techniques, e.g., of polycarbonate and/or ABS. Stylet 55, cannula 21, first 24 and second 25 compression springs can be formed of stainless steel.

The term "patient" includes all animals, human or non-human. Examples include birds, reptiles, amphibians, and mammals, e.g., humans, other primates, pigs, rodents such as mice and rats, rabbits, guinea pigs, hamsters, cows, horses, cats, dogs, sheep and goats. Preferred patients are humans, farm animals, and domestic pets such as cats and dogs.

The biopsy instrument can be used for sampling in any part of a body, e.g., stomach, colon, rectum, mouth/pharynx, esophagus, larynx, liver, pancreas, lung, breast, cervix uteri, corpus uteri, ovary, prostate, testis, bladder, skin, kidney, brain/central nervous system, head, neck and throat, among others.

A number of embodiments of the invention have been described. Nevertheless, it will be understood that various modifications may be made without departing from the spirit and scope of the invention. Accordingly, other embodiments are within the scope of the following claims.

What is claimed is:

1. A medical instrument, comprising:
   a housing;
   a stylet having a portion in the housing;
   a movable first member in the housing, the first member being connected to the stylet; and
   a second member located in the housing to reduce movement of the first member, the second member in contact with and extending axially from the stop, the second member configured to change movement of the first member from a linear first direction to a second direction that has a component transverse to the first direction.

2. The instrument of claim 1, wherein the second member comprises a raised portion configured to contact the first member.

3. The instrument of claim 2, wherein the raised portion is disposed off-center relative to a longitudinal axis of the instrument.

4. The instrument of claim 1, wherein the housing comprises a recessed portion capable of accommodating a portion of the first member.

5. The instrument of claim 4, wherein the recessed portion is on a side wall of the housing.

6. The instrument of claim 1, further comprising a cannula having a portion in the housing, and a movable third member connected to the cannula, wherein the second member is between the first member and the third member.

7. The instrument of claim 6, further comprising a pivotable latch capable of holding and releasing the movable third member.

8. The instrument of claim 1, further comprising a pivotable latch capable of holding and releasing the movable first member.

9. The instrument of claim 8, further comprising a first trigger capable of engaging the pivotable latch to release the movable first member.

10. The instrument of claim 9, further comprising a second trigger capable of engaging the pivotable latch to release the movable first member.

11. A medical instrument, comprising:
    a housing;
    a movable stylet block in the housing;
    a stylet connected to the stylet block;
    a movable cannula block in the housing;
    a cannula connected to the cannula block; and
    a stop between the stylet block and the cannula block, the stop configured to contact the stylet block off-centered relative to a center longitudinal axis of the medical instrument, the stop comprising a first portion and a second portion, the second portion extending in a direction parallel to the longitudinal axis from the first portion.

12. The instrument of claim 11, wherein the stop comprises a raised portion configured to contact the stylet block off-centered.

13. The instrument of claim 11, wherein the housing comprises a recessed portion configured to accommodate a portion of the stylet block.

14. The instrument of claim 11, further comprising a pivotable latch capable of holding and releasing the cannula block.

15. The instrument of claim 11, further comprising a pivotable latch capable of holding and releasing the stylet block.

16. The instrument of claim 15, further comprising two triggers, either trigger capable of pivoting the latch to release the stylet block.

* * * * *